United States Patent [19]
Harrington et al.

[11] Patent Number: 5,472,670
[45] Date of Patent: Dec. 5, 1995

[54] GAS CHROMATOGRAPHY SAMPLE INJECTOR AND APPARATUS USING SAME

[75] Inventors: Peter de B. Harrington; Hans P. Whittenberg, both of Athens, Ohio

[73] Assignee: Ohio University, Athens, Ohio

[21] Appl. No.: 27,282

[22] Filed: Mar. 5, 1993

[51] Int. Cl.$^6$ .................................................. G01N 30/02
[52] U.S. Cl. ............................ 422/89; 436/161; 436/173; 73/23.41; 73/23.42; 250/425
[58] Field of Search ............................ 422/89; 436/161, 436/173, 177, 181; 73/23.41, 23.42; 250/288, 425

[56] References Cited

U.S. PATENT DOCUMENTS

| | | | |
|---|---|---|---|
| 4,124,358 | 11/1978 | Müller | 55/67 |
| 4,408,125 | 10/1983 | Meuzelaar | 250/288 |
| 4,980,131 | 12/1990 | Meuzelaar et al. | 422/78 |
| 5,150,601 | 9/1992 | Simeroth et al. | 73/23.41 |

OTHER PUBLICATIONS

Barbour, William M. "Refinement of Pyrolysis Techniques for Gas Chromatography" *J. of G.C.,* Jul. 1965, pp. 228–231.
Berezkin, V. G. "The Development of Pyrolysis Gas Chromatography." *CRC Critical Reviews in Analytical Chemistry,* Mar. 1981, pp. 1–25.
Levy, R. L. "Trends and Advances in Design of Pyrolysis Units for Gas Chromotography" *J. of G.C.,* Jul. 1965, pp. 228–231.
Levy, R. L. *Pyrolysis Gas Chromatography,* pp. 49∝85.
Morgan, Stephen L. and Jacques, Christopher A. "Characterization of Simple Carbohydrate Structure by Glass Capillary Pyrolysis Gas Chromatography and Cluster Analysis" *Analytical Chemistry,* vol. 54, No. 4, Apr. 1982, pp. 741–747.
Sahota, Rachhpal S. and Morgan, Stephen L. "Vector Representation, Feature Selection, and Fingerprinting: An Application of Pattern Recognition to Pyrolysis–Gas Chromatography/Mass Spectrometry of Nucleosides" *Analytical Chemistry,* vol. 65, No. 1, Jan. 1, 1993, pp. 70–77.
Whiton, Robert S. and Morgan, Stephen L. "Modified Interface for Pyrolysis Gas Chromotography with Capillary Columns" *Analytical Chemistry,* vol. 57, No. 3, Mar. 1985, pp. 778–780.

*Primary Examiner*—David A. Redding
*Attorney, Agent, or Firm*—John L. Gray

[57] ABSTRACT

The present invention relates to an improved sample injector for use in gas chromatography. The invention also includes a method of injecting a sample onto a chromatographic column, and a method of analyzing a sample using column chromatography and/or mass spectrometry. The improved sample injector features an arrangement to allow a pyrolytic probe to be more easily inserted into the vaporization cavity while permitting the sample to be volatilized in such a way that the sample is more efficiently introduced onto the column. Another feature of the invention is the use of means to reduce the volume of the pyrolysis/vaporization cavity so as to provide efficient throughput of pure sample. Also part of the present invention is a gas chromatograph and gas chromatograph-mass spectrometer which uses the sample injector of the present invention. The present invention includes methods of sample injection and sample analysis using the aforementioned apparatus of the present invention.

19 Claims, 3 Drawing Sheets

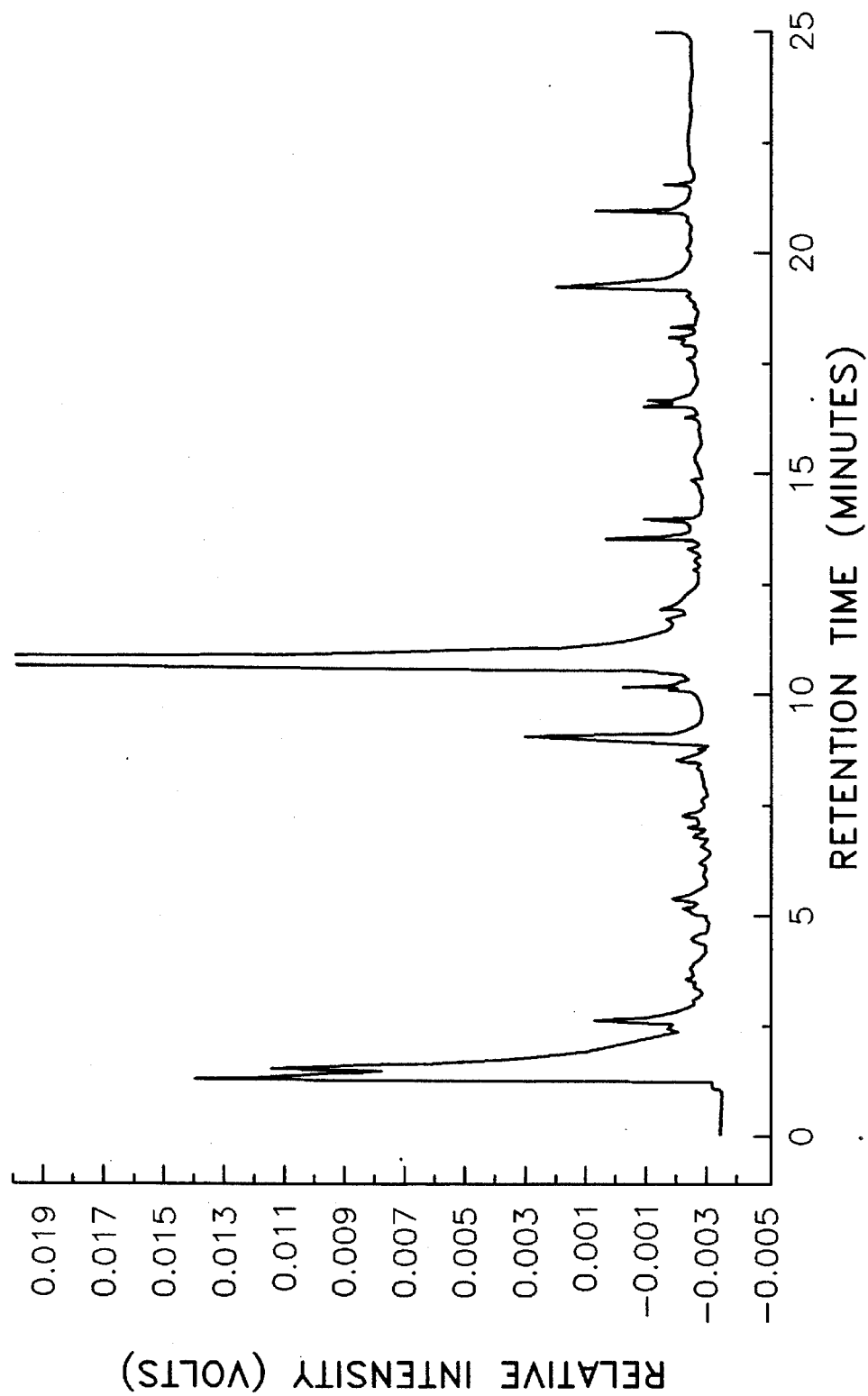

GAS CHROMATOGRAPHY SAMPLE INJECTOR AND APPARATUS USING SAME

TECHNICAL FIELD

The present invention relates to an improved sample injector for use in gas chromatography. The invention also includes a method of injecting a sample onto a chromatographic column, and a method of analyzing a sample using column chromatography and/or mass spectrometry. The improved sample injector features an arrangement to allow a pyrolytic probe to be more easily inserted into the vaporization cavity while permitting the sample to be volatilized in such a way that the sample is more efficiently introduced onto the column. Another feature of the invention is the use of means to reduce the volume of the pyrolysis/vaporization cavity so as to provide efficient throughput of pure sample. Also part of the present invention is a gas chromatograph and gas chromatograph-mass spectrometer which uses the sample injector of the present invention. The present invention includes methods of sample injection and sample analysis using the aforementioned apparatus of the present invention.

BACKGROUND

In the field of gas chromatography, one of the critical areas where events leading to analytic errors can occur is at the interface between the chromatographic column and the sample injector. There are several events surrounding the injection of sample which can lead to sample loss or less than ideal sample injection.

Gas chromatography of the type to which the invention pertains generally comprise a pyrolysis/volatilization chamber in which the sample is pyrolyzed or otherwise volatilized before being conducted onto the chromatographic column.

One such type of gas chromatograph are those used in the field of pyrolysis (Py)-gas chromatography (GC), particularly high resolution gas chromatography (HRGC), and Py-GC-mass spectrometry (MS). An example of the use of Py-GC-MS is described for instance in Holzer, et al., *Analysis of In Situ Methylated Microbial Fatty Acid Constituents By Curie-Point Pyrolysis-Gas Chromatography-Mass Spectrometry*, J. of Chrom., vol. 48, pp. 181–190 (1989), hereby incorporated herein by reference. This technique has developed into a widely accepted technique which is particularly powerful in the analysis of non-volatile materials, such as high molecular weight organic compounds, synthetic polymers and complex biological materials. Thermal degradation of these substances generate a large variety of decomposition products, which range from chemically related isomers to compounds that differ in polarity, structure and molecular mass. The diverse chemical nature of the decomposition products demands rigid standards for the analytical system. Furthermore, the samples to which this technique is applied are often very small, putting the preservation of sample and efficient and concentrated sample introduction onto the column at a premium.

With respect to the preservation of sample, small quantities of sample usually must be placed on a heating element, such as a resistive filament type pyrolyzer, or ferromagnetic Curie-point pyrolyzer probe, and introduced into the environmentally isolated pyrolysis/ volatilization chamber. This process is difficult because the filament/probe must be inserted through a septum (used to protect the column environment) which can disturb the sample, causing sample loss or spreading of the sample over the surface of the filament/probe which can disturb he uniformity of presentation of the volatile products to the chromatographic column.

Another problem in the injection of volatilized material onto a chromatographic column is the difficulty in maintaining the uniform concentration of volatilized analyte supplied to the column. One factor pertaining to this problem is the condensation of volatilized analyte upstream of the chromatographic column. Some injector systems actually are designed to facilitate such condensation through the use of an inert support material in the path of the volatilized sample products. Condensation of the volatilized sample products can diminish the amount of material actually reaching the column, as well as generally disrupting the regularity of flow of analyte to the column and even possibly rendering the mixture of the volatilized sample products reaching the column non-uniform with respect to product mix. Therefore it is desirable to produce an injector which efficiently and uniformly supplies volatilized sample products to the chromatographic column.

Pyrolytic reproducibility and the minimization of secondary reactions, to optimize resolution through rapid sample introduction, are also desirable characteristics in GC and GC-MS systems.

As mentioned above, chromatographic columns are often used in conjunction with a detector and/or a mass spectrometer. In calibrating such systems, pure samples are often injected. In such cases, is desirable to be able to efficiently throughput amounts of pure sample from a chromatographic column. In the case of mass spectrometers, calibration normally must be carried out by use of a direct insertion probe (DIP). To use the DIP, a second, auxilliary inlet must be used to insert the DIP inserted into the vacuum chamber of the mass spectrometer. This insertion poses a risk that the vacuum of the instrument might be broken and the spectrometer contaminated. Accordingly, it is also desirable to be able to produce a GC-MS system capable of operating in both a classical GC-MS analytical mode and a rapid pure sample through mode, without the need to disassemble the GC-MS and risk contamination or damage to the instrument.

The general function of a high pressure (HP) split/splitless injector or any other model split/splitless injector is to deliver a small volume (several nanoliters) onto a high resolution capillary column. This small volume is necessary to avoid overloading high resolution capillary columns with sample capacities in the range of 10–75 nanograms.

Unfortunately, the lower limit on syringe volume is in the microliter range (1000 nanoliters) so the sample must be reduced in volume to introduce it onto the column in a narrow band which is very important in high resolution GC. This is accomplished by splitting the sample in a ratio of 1:100 or 1:10000 where the first number is the amount introduced onto the column and the second number is the amount vented to the atmosphere by the split injector. As pointed out above, one disadvantage of this technique is loss of sample which may only be present in trace amounts. Another major disadvantage is that quite often the composition of the split sample does not reflect the actual composition of the original sample thereby making quantitative work difficult. This is especially true when the components of the sample encompass a wide range of boiling points.

The splitless mode of injectors allows for entire sample introduction onto the column. However, it is often difficult to place a sample onto a column when a relatively large amount of solvent accompanies the analyte as is typically the case. The first technique commonly used to separate the solvent is known as cold trapping. This method typically requires recondensation of the sample at the beginning of the column. The sample will be introduced much more slowly onto the column but will not spread out very far due to the fact that the liquid will become immobilized and the volume of the liquid is much less than the volume of the gas. Recondensation is accomplished by keeping the temperature twenty degrees below the boiling point of the least volatile component. The temperature is slowly raised to volatilize the compounds trapped at the beginning of the column.

Another technique used to deal with this large amounts of solvent is the use of the solvent effect method. In this method the solvent is recondensed at the beginning of the column and the analyte is introduced and dissolves into the liquid solvent. The temperature is then slowly raised to allow the sample components to elute off the column. Both of these techniques are used to when sample volumes larger then the capacity of the column are injected.

Accordingly, it is desirable to be able produce an injector which is capable of introducing a sample onto a chromatographic column without recondensation of the sample by cold trapping, or the use of solvent effect recondensation.

Of course, such solvent-based injection techniques are only applicable to the injection of solvated analytes. Thus, it is also desirable to be able to produce an injector capable of injecting samples where it is impossible or undesirable to use solvent, such as in the case of insoluble samples or samples in very small quantities.

The present invention is most applicable to the fields of biochemistry, biotechnology, food science, forensic science and environmental monitoring.

In view of the disclosure of the present invention and from the practice thereof, additional advantages and the solution to other problems may become apparent to one of ordinary skill in the art.

SUMMARY OF THE INVENTION

The present invention includes an apparatus for pyrolyzing a sample and injecting the sample into a gas chromatograph, the gas chromatograph having a chromatographic column, the chromatographic column defining an inside and outside thereof, and having an inlet, the apparatus comprising: (a) an injector body having a cavity and only three openings, the three openings consisting of: (1) a first opening connecting the cavity to the inlet of the chromatographic column, (2) a second opening connecting the cavity to the outside of the chromatographic column, and (3) a carrier gas inlet; and (b) pyrolyzing means for pyrolyzing the sample, the pyrolyzing means being disposed within the cavity, there being a sufficiently unobstructed path between the pyrolyzing means whereby, the vaporization product(s) enter(s) the chromatographic column substantially without condensing.

As used herein with respect to gas chromatography, pyrolysis and pyrolyzing refers to the decomposition and vaporization of a sample in an inert atmosphere. Pyrolysis is typically carried out at temperatures above 300° C., typically in the range of 300° C. to 900° C. Pyrolysis is also characterized by relatively rapid heating wherein the sample is brought to pyrolytic temperature within a very short time, generally less than one second, typically within one to one hundred milliseconds.

Reference to vaporization or vaporizing with respect to gas chromatography is intended to mean the process by which a substance is converted into a vapor, and may include both pyrolytic vaporization (brought about in pyrolysis) and non-pyrolytic vaporization. Non-pyrolytic vaporization is normally carried out at relatively low temperatures, typically below 300° C., and over time periods extending over several minutes for solvated samples injected using known techniques.

As used herein, high temperature vaporization refers to vaporization which is carried out within one second, typically within one to one hundred milliseconds, and normally at temperatures above 300° C. for samples of the size typically used in gas chromatography. High temperature vaporization is normally what occurs when volatile samples in amounts typically used in gas chromatography are volatilized at temperatures normally used to pyrolyze non-volatile samples, i.e. 300° C. to 900° C.

The pyrolyzing means used in accordance with the present invention may be any pyrolyzing means appropriate for use in gas chromatography, such as a pyrolytic resistive filament or a Curie-point pyrolytic probe, or their functional equivalent. Pyrolyzing means also includes means for bringing about high temperature vaporization of volatile samples as described above.

The chromatographic column may be any type of column used in the field of gas chromatography, such as a high resolution capillary column, using flow rates of ½ ml/min. to 4 ml/min.

The present invention also includes an analytical apparatus for pyrolyzing and analyzing a sample by gas chromatography, and which includes the an injector in accordance with the present invention. The analytical apparatus of the present invention comprises: (a) a chromatographic column, the chromatographic column defining an inside and an outside thereof, and having an inlet and an outlet; (b) an injector apparatus, the apparatus comprising an injector body having a cavity, the cavity having only three openings, the three openings consisting of: (1) a first opening connecting the cavity to the chromatographic column, (2) a second opening connecting the cavity to the outside of the chromatographic column and (3) a carrier gas inlet; (c) pyrolyzing means for pyrolyzing the sample so as to produce at least one vaporization product of the sample, the pyrolyzing means being disposed within the cavity, there being a sufficiently unobstructed path (preferably a completely unobstructed path) between said pyrolyzing means and said inlet whereby the vaporization product(s) of the sample enter(s) the chromatographic column substantially without condensing; and (d) analyzing means disposed at the outlet.

The chromatographic column used in the analytical apparatus of the present invention may be any column appropriate for use in gas chromatography such as a high resolution capillary column.

The analyzing means used in the present invention may include such analyzing means as a detector capable of detecting the vaporization product(s) of the sample, such as a thermocouple detector, a photocell detector, an electron capture detector, or their functional equivalent, and may also include a mass spectrometer.

In addition to the above-described apparatus of the present invention, the present invention also includes a method of pyrolyzing a sample in preparation for subjecting a sample to gas chromatography using a chromatographic column, the chromatographic column defining an inside and an outside, and having an inlet, the method comprising the steps of: (a) obtaining an amount of the sample to be pyrolyzed; (b) pyrolyzing substantially all of the amount of the sample in an isolated space so as to form at least one vaporization product of the sample, such at least one vaporization product being at an initial concentration, (c) conducting substantially all of the vaporization product(s) from the isolated space and into the chromatographic column substantially without condensing.

The vaporization of the sample may be carried out by any method appropriate to gas chromatography such as by resistive filament heating pyrolysis or Curie-point pyrolysis.

It is preferred that the method of the present invention be carried out on a sample that is less than 100 nanograms. It is also preferred that the amount of sample be selected so as to yield a volume of the sample vaporized in the pyrolyzing step is less than 1 microliter.

The present invention also includes a method of analyzing a sample by gas chromatography using a chromatographic column, the chromatographic column defining an inside and an outside, and having an inlet, the method comprising the steps of: (a) obtaining an amount of a sample to be analyzed; (b) pyrolyzing substantially all of the amount of the sample in isolation from the outside of the chromatographic column so as to form one or more vaporization product of the sample, the vaporization product(s) having an initial mass, (c) introducing substantially the entire mass of the vaporization product(s) into the chromatographic column without allowing the vaporization product(s) to condense; (d) causing the vaporization product(s) to issue from the chromatographic column; and (e) analyzing the vaporization product(s) issuing from the chromatographic column.

The pyrolyzing of the sample may be carried out by any method appropriate to gas chromatography such as by resistive filament heating pyrolysis and Curie-point pyrolysis.

It is preferred that substantially all of the amount of the sample is introduced into the chromatographic column.

Although any column appropriate for use in the field of gas chromatography may be used, it is preferred that the chromatographic column be a high resolution capillary column.

The analysis of the vaporization product(s) issuing from the chromatographic column may be carried out by the use of any detection or analyzing means used in gas chromatography, such as a photocell detector, a thermocouple detector or electron capture detector. Analysis may also be carried out by mass spectrometry.

The present invention also includes an apparatus for injecting a sample into a gas chromatograph, the gas chromatograph having a vaporization cavity and chromatographic column, the chromatographic column defining an inside and outside thereof, and having an inlet, the apparatus comprising: (a) an injector body having a vaporization cavity and only three openings, the three openings consisting of: (1) a first opening connecting the cavity to the inlet of the chromatographic column, (2) a second opening connecting the cavity to the outside the chromatographic column, the second opening closed by a resilient pierceable septum, and (3) a carrier gas inlet; (b) a hollow tube capable of being moved from a first position outside the chromatographic column through the septum to a second position wherein at least a portion of the hollow tube extends inside the cavity whereby the hollow tube creates a passageway through the septum from the outside of the chromatographic column to the vaporization cavity; and (c) a sample vaporization probe adapted to carry the sample and dimensioned so as to be extendable through the hollow tube while the hollow tube is in the second position, to a position wherein the sample probe extends into the vaporization cavity.

The hollow tube may be any tube appropriate to the use in accordance with the present invention. The hollow tube may be in the form of a syringe needle.

The sample probe may be any object capable of being extended through the hollow tube of the present invention, such as in the form of a wire. For example, ferromagnetic wires may be used in cases where sample vaporization is to be carried out by Curie-point pyrolytic heating, while resistive heating wires may be used in cases where sample vaporization is to be carried out by resistant heating.

The invention also includes an apparatus for vaporizing a sample and injecting the sample into a gas chromatograph, the gas chromatograph having a chromatographic column, the chromatographic column defining an inside and outside thereof, and having an inlet, the apparatus comprising: (a) an injector body having a vaporization cavity and only three openings, the three openings consisting of: (1) a first opening connecting the cavity to the inlet of the chromatographic column, (2) a second opening connecting the cavity to the outside the chromatographic column, the second opening closed by a resilient pierceable septum and (3) a carrier gas inlet; and (b) a hollow tube capable of being moved from a first position outside the chromatographic column through the septum to a second position wherein at least a portion of the hollow tube extends inside the cavity whereby the hollow tube creates a passageway through the septum from the outside of the chromatographic column to the vaporization cavity; (c) a sample vaporization probe adapted to carry the sample and dimensioned so as to be extendable through the hollow tube while the hollow tube is in the second position, to a position wherein the sample probe extends into the vaporization cavity; and (d) vaporizing means for vaporizing the sample within the vaporization cavity.

The vaporizing means may be selected from any means appropriate to gas chromatography, such as Curie-point pyrolytic probes and resistive pyrolytic filaments, or other filaments adapted to vaporize a sample.

The invention also comprises an apparatus for vaporizing a sample and injecting the sample into a gas chromatograph, the gas chromatograph having a chromatographic column, the chromatographic column defining an inside and outside thereof, and having an inlet, the apparatus comprising: (a) an injector body, the injector body having a cavity defining a volume and having only three openings, the three openings consisting of: (1) a first opening connecting the cavity to the inlet of the chromatographic column, (2) a second opening connecting the cavity to the outside of the chromatographic column and (3) a carrier gas inlet; (b) mechanical means adapted to vary the volume of the cavity; and (c) vaporizing means for vaporizing the sample, the vaporizing means being disposed within the cavity, there being a sufficiently unobstructed path between the vaporizing means and the inlet whereby the vaporization product(s) enter(s) the chromatographic column substantially without condensing.

For use with most high resolution gas chromatographic columns, it is preferred that the mechanical means be adapted to reduce the volume of said cavity to a volume below about 1.5 milliliters.

The mechanical means used in the present invention may be any mechanical means capable of varying the volume of the vaporization cavity. Such means preferably may be a removable sleeve adapted to be moved from a position outside the cavity to a position inside the cavity. The mechanical means preferably comprises a material on its cavity-facing surface(s) (such as the inner surface of a sleeve) such that the cavity defined thereby is provided with an inert material which will not react with volatilization products. Such material may include a deactivated glass sleeve which is deactivated by treatment with trimethylsilane chloride (TMSCl). Other equivalent mechanical means adapted to reduce the volume of the cavity may also be used, such as equivalent space-occupying or -diminishing arrangements having inert surfaces exposed to the vaporization cavity.

Optionally and preferably, the vaporizing means comprises pyrolyzing means capable of yielding at least one pyrolysis product of the sample to be analyzed.

The present invention also features a dual mode analytical apparatus for vaporizing and analyzing a sample by gas chromatography. The dual mode analytical apparatus comprises: (a) a gas chromatographic column defining an inside and an outside thereof, and having an inlet and an outlet; (b) an injector body, the injector body having a cavity defining a volume and having at least three openings comprising: (1) a first opening connecting the cavity to the inlet of the chromatographic column, (2) a second opening connecting the cavity to the outside of the chromatographic column; (c) a carrier gas inlet; (d) mechanical means adapted to vary the volume of the cavity; and (e) vaporizing means for vaporizing the sample so as to form at least one vaporization product of the sample, the vaporizing means being disposed within the cavity, there being a sufficiently unobstructed path between the vaporizing means and the inlet whereby the at least one vaporization product enters the chromatographic column substantially without condensing; and analyzing means disposed at the outlet.

For use with most high resolution gas chromatographic columns, it is preferred that the mechanical means be adapted to reduce the volume of said cavity to a volume below about 1.5 milliliters.

The mechanical means used in the present invention may be any mechanical means capable of varying the volume of the vaporization cavity. Such means preferably may be a removable sleeve adapted to be moved from a position outside the cavity to a position inside the cavity. The mechanical means preferably comprises a material on its cavity-facing surface(s) (such as the inner surface of a sleeve) such that the cavity defined thereby is provided with an inert material which will not react with volatilization products. Such material may include a deactivated glass sleeve which is deactivated by treatment with trimethylsilane chloride (TMSCl). Other equivalent mechanical means adapted to reduce the volume of the cavity may also be used, such as equivalent space-occupying or diminishing arrangements having inert surfaces exposed to the vaporization cavity.

Optionally and preferably, the vaporizing means comprises pyrolyzing means capable of yielding at least one pyrolysis product of the sample.

The analyzing means comprises a detector capable of detecting the vaporization product(s) of the sample, the detector selected from the group consisting of photocell detectors, thermocouple detectors and electron capture detectors. The analyzing means may also include a mass spectrometer.

As a type of dual mode analytical apparatus of the present invention, the present invention also specifically includes a dual mode gas chromatograph—mass spectrometer which comprises: (a) a gas chromatographic column; (b) an apparatus for vaporizing a sample and injecting the sample into the gas chromatographic column, the gas chromatographic column defining an inside and outside thereof, and having an inlet, the apparatus comprising: (1) an injector body, the injector body having a cavity defining a volume and having only three openings, the three openings consisting of: (i) a first opening connecting the cavity to the inlet of the chromatographic column, (ii) a second opening connecting the cavity to the outside of the chromatographic column and (iii) a carrier gas inlet; (c) mechanical means adapted to vary the volume of the cavity; (d) vaporizing means for vaporizing the sample so as to form at least one vaporization product of the sample, the vaporizing means being disposed within the cavity, there being a sufficiently unobstructed path between the vaporizing means and the inlet whereby the vaporization product(s) of the sample enter(s) the chromatographic column substantially without condensing; and (e) a mass spectrometer. It is also preferred that the injector cavity be maintained at a sufficiently high temperature to help maintain the vaporization products in a gaseous state.

DESCRIPTION OF THE DRAWINGS

FIG. 3 is another typical chromatogram obtained from the pyrolysis of polystyrene using the present invention.

DETAILED DESCRIPTION OF THE PREFERRED EMBODIMENT

In accordance with the foregoing summary of the invention, the following describes a preferred embodiment of the present invention which is presently considered to represent the best mode of the invention.

Figure 1:
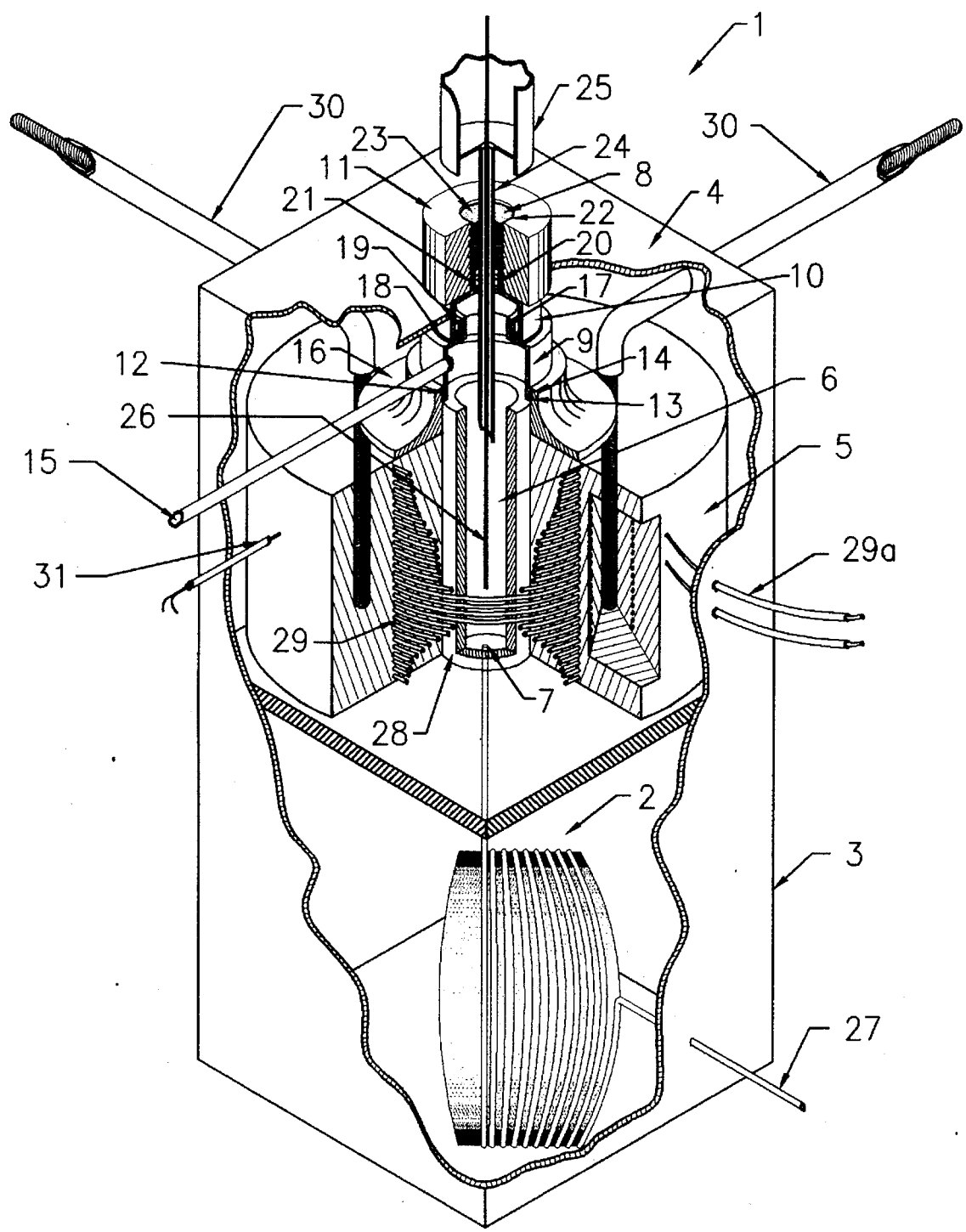
FIG. 1 is a sectioned perspective view of a gas chromatograph and an injector in accordance with one embodiment of the present invention.

FIG. 1 shows a sectioned perspective view of a gas chromatograph and an injector in accordance with this embodiment of the present invention.

FIG. 1 shows gas chromatograph 1 which comprises a high resolution gas chromatographic column 2 housed in a typical constant temperature container 3.

The chromatographic column 2 is served by injector 4 which comprises a splitless ceramic injector body 5 having an injector cavity 6 which has only three openings: a first opening 7 connecting the cavity 6 to the inlet of the chromatographic column 2; a second opening 8 connecting the cavity 6 to the outside of the chromatographic column 2 (opened and closed by action of a septum as described below), and a carrier gas inlet 15.

The second opening 8 extends through carrier gas fitting 9, adapter piece 10 and through cap piece 11. Carrier gas fitting 9 is provided with threading 12 and O-ring 13 adapted to fit into the threading 14 in base fitting 16. Carrier gas fitting 9 also has threading 17 and O-ring 18 so as to be attached and sealed to adapter piece 10 via threading 19. Adapter piece 10 in turn has threading 20 which allows it to be attached and sealed to cap piece 11 via threading 21. Cap piece 11 has aperture 22 and resilient pierceable septum 23 in the form of a Teflon® or Teflon® rubber septum which is disposed beneath cap piece 11 and exposed by aperture 22. Resilient pierceable septum 23 may be made of any pierceable resilient material which is capable of closing the second opening to isolate the injector cavity 6 from the outside of the column 2, while being capable of being opened by piercing by a hollow tube, such as syringe needle 24 having metal fitting 25.

The injector also comprises a Curie point probe 26 which pyrolyzes the sample so as to produce vaporization product(s) of the sample. As can be appreciated from FIG. 1, there is maintained a sufficiently unobstructed path between the Curie point probe 26 and the inlet 7 whereby the vaporization product(s) of the sample enter(s) the chromatographic column 2 substantially without condensing.

The chromatographic column 2 is connected via outlet 27 to a standard detector and/or mass spectrometer.

The Curie point method of induction heating is used in this apparatus to pyrolyze the sample. In this method, a microgram or less of sample is coated onto a ferromagnetic wire which is heated by induction within a second to an exact temperature specified by the wire composition. This method is ideal for splitless injection because the sample is introduced rapidly thereby minimizing band broadening and improving resolution. For splitless injection a quantity in the nanogram range is coated onto the wire to avoid overloading the columns which have a capacity ranging from 10–75 nanograms. This small sample size also serves to minimize the collisions between the pyrolysis products.

In a preferred embodiment, the Curie point probe 26 is surrounded by a removable deactivated glass tube 28 which is approximately 1.2 mL in volume. Without this relatively smaller glass sleeve, i.e. using a standard glass-walled cavity, the relatively large volume relative to the size of the sample serves several purposes. The main purpose of the large volume is to allow adequate space for the expansion of the pyrolysis products and also to allow for sufficient flow for the pyrolyzates to be rapidly swept onto the column and away from the heated zones in the injector thereby minimizing the probability of secondary reactions occurring. The rapid clearing of the injector also ensures the sample is swept onto the column in a narrow bank which is important to optimize resolution in capillary chromatography.

Surrounding the deactivated glass sleeve 28 is the radio frequency (rf) coil 29 which induces heating in the Curie point probe 26. The rf coil 29 also contains a 10 V AC heating elements 30 to prevent recondensation of the pyrolyzates in the inlet system. The temperature may be monitored for instance by thermocouple 31 shown imbedded in splitless ceramic injector body 5.

The connection to the column is made at the bottom of the injector cavity 6 and the carrier gas enters through an inlet 15 at the top of the injector cavity 6.

By decreasing dead volume of the injection system with the glass sleeve, a second application was generated. A novel injection system was obtained that yielded rapid introduction of high molecular weight compounds into a mass spectrometer. This injection method has broad application, because HRGC systems with mass spectrometer (MS) detectors are widely used. To directly analyze compounds a second inlet system is required (i.e., direct insertion probe (DIP)). The sample is directly inserted into the MS by breaking the MS vacuum, which places the instrument at risk. If the instrument is opened to the atmosphere, then it could be severely damaged.

The new injection system of the present invention allows for dual functionality. Samples may be pyrolyzed and chromatographically separated, or they may be directly analyzed by sliding in a sleeve (such as deactivated glass insert 28) that reduces the dead volume. Although not limited by the theory of action, it is believed that, in this latter mode, a pressure pulse is generated in the carrier gas that rapidly forces a high molecular weight sample through the column in times which are significantly less than normal retention times for such compounds (typically in times less than 1 minute). For instance, it has been found that pure compounds such as benzene can be put through a high resolution column within significantly reduced retention times. Such pure compounds can then be conducted into a mass spectrometer without having to use a direct insertion probe. No damage occurs to the column and the MS vacuum is preserved.

This injector will extend the range of application for HRGC/MS, in all fields with special impact on environmental and biotechnology for which analysis of nonvolatile samples is routine. The injector is easy to use and portable. The injector yields reproducible chromatograms.

A further advantage of splitless injection is that the entire sample is introduced onto the column. This has an advantage over split injection in that the injection process is non-descriminative making the splitless method more conducive to quantitative analysis. The performance and reproducibility of this system was evaluated by pyrolyzing polystyrene.

Experimental Results

Chemicals: A solution of $4\times10^{-7}$ g/mL of polystyrene in toluene was prepared.

Chromatographic instruments and conditions: The gas chromatograph used in this experiment was a Varian 3400 equipped with a flame ionization detector and interfaced to a Varian GC Star Integrator. Chromatography was carried out on a 30 m×0.32 mm internal diameter Restek RTX TG-65 column. The pyrolysis electronics were manufactured by Pyrotek of Boulder, Colo. A digital flow controller was used to regulate the flow of helium which was used as the carrier gas.

Procedure: A uL of the polystyrene solution was coated onto a one cm portion of the pyrolysis wire and the solvent allowed to evaporate. The sample was then inserted into the injector and heated for four seconds at 770° C. The sample was pyrolyzed at thirty seconds into the run. The column temperature was held at 50° C. for two minutes and programmed at 7° C. per minute to 225° C. The exact same experiment was repeated four times for reproducibility using a new wire. The carrier gas linear velocity was set at 4.10 ml/minute.

RESULTS AND DISCUSSION

Figure 2:
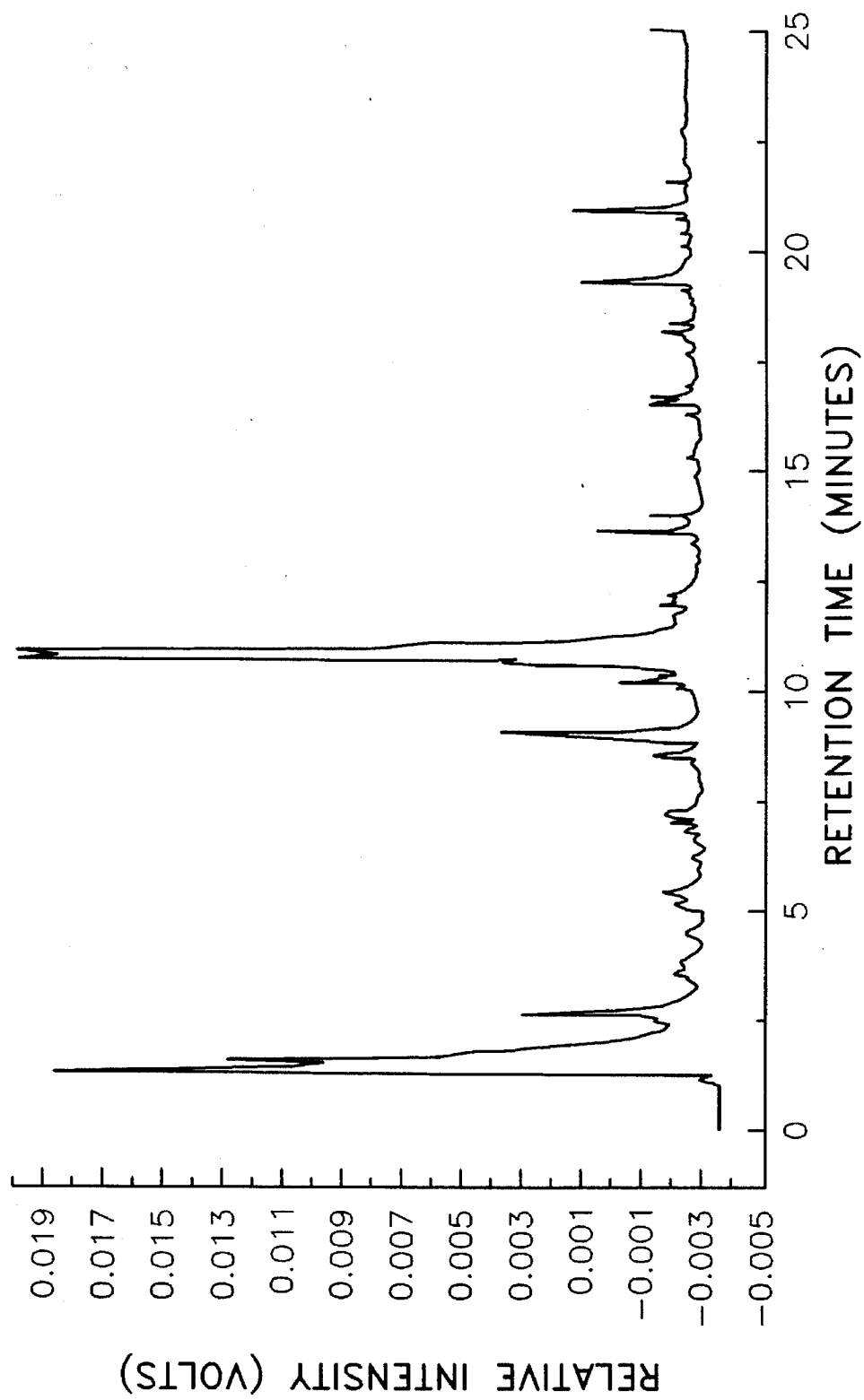
FIG. 2 is a typical chromatogram obtained from the pyrolysis of polystyrene using the present invention.

FIGS. 2 and 3 are typical chromatograms obtained form the pyrolysis of polystyrene using the present invention.

The following Table 1 further illustrates the chromatographic and pyrolytic reproducibility of this system and the usefulness of pyrolysis as an analytical tool.

Listed below are the retention times six of the structural fragments characteristic of polystyrene obtained from five different experiments under conditions identical to those listed above. The peaks used are designated in the above chromatogram. The peak at 16.5 minutes is the later eluting peak of the two between 16 and 17 minutes.

TABLE 1

| Run # | Peak 1 | Peak 2 | Peak 3 | Peak 4 | Peak 5 | Peak 6 |
|---|---|---|---|---|---|---|
| 1 | 1.567 | 2.607 | 8.888 | 16.488 | 19.279 | 21.021 |
| 2 | 1.549 | 2.614 | 9.048 | 16.469 | 19.286 | 20.922 |
| 3 | 1.566 | 2.625 | 9.037 | 16.488 | 19.304 | 20.944 |
| 4 | 1.549 | 2.612 | 8.96 | 16.505 | 19.281 | 20.953 |
| 5 | 1.545 | 2.615 | 9.042 | 16.493 | 19.313 | 20.947 |
| Average | 1.5552 | 2.6146 | 8.995 | 16.4886 | 19.2926 | 20.9574 |

TABLE 1-continued

| Run # | Peak 1 | Peak 2 | Peak 3 | Peak 4 | Peak 5 | Peak 6 |
| --- | --- | --- | --- | --- | --- | --- |
| Std. Dev. | 0.0104499 | 0.0065803 | 0.0697424 | 0.0129736 | 0.0150706 | 0.0374354 |
| Rel. Dev. | 0.0067193 | 0.0025167 | 0.0077535 | 0.0007807 | 0.0007801 | 0.0017806 |

The average, standard deviation, and relative deviation of the retention times of pyrolysis fragments are characteristic of polystyrene obtained from five identical experiments.

The above chromatograms and table illustrate that good quantitative and qualitative pyrolytic reproducibility can be obtained using a splitless injection system as long as the column is not overloaded. Further advantages of this system include high resolution, excellent sensitivity, non-descriminative analysis, and the ability to operate at high flow rates and temperatures. It was determined that the best results were obtained by coating the sample as evenly as possible on the portion of the wire heated by the induction coil and also using a clean wire for each experiment. Ensuring that the solvent evaporated entirely also improved reproducibility as did high flow rates through the inlet.

Even though a system may be optimized to facilitate reproducibility, the physical process of pyrolysis is very sensitive to experimental conditions so much attention must be paid to these parameters to obtain reproducible and scientifically meaningful results.

The following references relating generally to gas chromatography are hereby incorporated herein by reference:
1. V. G. Berezkin. Pyrolysis Gas Chromatography. *CRC Crit. Rev. Anal. Chem.* 1 (1981).
2. R. L. Levy. Trends and Advances in Design of Pyrolysis Units for Gas Chromatography. *J. Gas Chromatography.* 5:107 (1967).
3. R. L. Levy. Developments in Pyrolysis Gas Chromatography. *Chromatographic Reviews.* 8:48 (1966).
4. Douglas A. Skoog. *Principles of Instrumental Analysis*, 3rd. ed. Saunders Publishing, New York, 1985, pg. 700–800.
5. K. J. Hyver and P. Saundra. *High Resolution Gas Chromatography*, Hewlett Packard Publishing, USA, 1989, Chapter 3.
6. Stephen L. Morgan and Robert S. Whiton. Modified Interface for Pyrolysis Gas Chromatography with Capillary Columns. *Anal. Chem.* 57:778 (1985).

In view of the foregoing disclosure or through practice of the present invention, it will be within the ability of one reasonably skilled in the art to make modifications to the present invention, such as through the use of equivalent materials and arrangements, without departing from the spirit of the invention as reflected in the appended claims.

What is claimed is:

1. An apparatus for injecting a sample into a gas chromatograph, said gas chromatograph having a vaporization cavity and a chromatographic column, said chromatographic column defining an inside and outside thereof, and having an inlet, said apparatus comprising:
   (a) an injector body having a cavity and at least three openings, said at least three openings comprising:
      (i) a first opening connecting said cavity to said inlet of said chromatographic column,
      (ii) a second opening connecting said cavity to said outside said chromatographic column, said second opening closed by a resilient pierceable septum, and
      (iii) a carrier gas inlet; and
   (b) a hollow tube capable of being moved from a first position outside said chromatographic column through said septum to a second position wherein at least a portion of said hollow tube extends inside said cavity whereby said hollow tube creates a passageway through said septum from said outside of said chromatographic column to said cavity;
   (c) a sample probe adapted to carry said sample and dimensioned so as to be extendable through said hollow tube while said hollow tube is in said second position, to a position wherein said sample probe extends into said cavity.

2. An apparatus according to claim 1 wherein said hollow tube is a syringe needle.

3. An apparatus according to claim 1 wherein said sample probe is selected from the group consisting of Curie-point pyrolytic filaments and resistive heating filaments.

4. An apparatus for vaporizing a sample and injecting said sample into a gas chromatograph, said gas chromatograph having a chromatographic column, said chromatographic column defining an inside and outside thereof, and having an inlet, said apparatus comprising:
   (a) an injector body having a cavity and at least three openings, said at least three openings comprising:
      (i) a first opening connecting said cavity to said inlet of said chromatographic column,
      (ii) a second opening connecting said cavity to said outside of said chromatographic column, said second opening closed by a resilient pierceable septum, and
      (iii) a carrier gas inlet; and
   (b) a hollow tube capable of being moved from a first position outside said chromatographic column through said septum to a second position wherein at least a portion of said hollow tube extends inside said cavity whereby said hollow tube creates a passageway through said septum from said outside of said chromatographic column to said cavity;
   (c) a sample probe adapted to carry said sample and dimensioned so as to be extendable through said hollow tube while said hollow tube is in said second position, to a position wherein said sample probe extends into said cavity; and
   (d) vaporizing means for vaporizing said sample within said vaporization cavity.

5. An apparatus according to claim 4 wherein said vaporizing means comprises a Curie-point pyrolytic heating means.

6. An apparatus according to claim 4 wherein said chromatographic column comprises a high resolution capillary column.

7. An apparatus according to claim 4 wherein said vaporizing means comprises pyrolyzing means.

8. An apparatus for vaporizing a sample and injecting said sample into a gas chromatograph, said gas chromatograph having a chromatographic column, said chromatographic column defining an inside and outside thereof, and having an inlet, said apparatus comprising:
   (a) an injector body, said injector body having a cavity defining a volume and having at least three openings, said at least three openings comprising:
      (i) a first opening connecting said cavity to said inlet of said chromatographic columns,
      (ii) a second opening connecting said cavity to said outside of said chromatographic column, and
      (iii) a carrier gas inlet; and
   (b) mechanical means adapted to vary the volume of said cavity; and (c) vaporizing means for vaporizing said sample so as to form at least one vaporization product of said sample, said vaporization means being disposed within said cavity, there being a sufficiently unobstructed path between said vaporization means and said inlet of said chromatographic column whereby said at least one vaporization product enters said chromatographic column substantially without condensing.

9. An apparatus according to claim 8 wherein said mechanical means is adapted to reduce the volume of said cavity to a volume below about 1.5 milliliters.

10. An apparatus according to claim 8 wherein said mechanical means comprises a sleeve adapted to be moved from a position outside said cavity to a position inside said cavity.

11. An apparatus according to claim 10 wherein said sleeve comprises a deactivated glass sleeve.

12. An apparatus according to claim 8 wherein said vaporizing means comprises pyrolyzing means and wherein said at least one vaporization product comprises at least one pyrolysis product.

13. An dual mode analytical apparatus for vaporizing and analyzing a sample by gas chromatography, said analytical apparatus comprising:

(a) a gas chromatographic column, said gas chromatographic column defining an inside and an outside thereof, and having an inlet and an outlet;

(b) an injector body, said injector body having a cavity defining a volume and having at least three openings, said at least three openings comprising:
  (i) a first opening connecting said cavity to said inlet of said chromatographic column,
  (ii) a second opening connecting said cavity to said outside of said chromatographic column, and
  (iii) a carrier gas inlet; and (c) mechanical means adapted to vary the volume of said cavity;

(d) vaporizing means for vaporizing said sample so as to form at least one vaporization product of said sample, said vaporizing means being disposed within said cavity, there being a sufficiently unobstructed path between said vaporizing means and said inlet whereby said at least one vaporization product enters said chromatographic column substantially without condensing; and (e) analyzing means disposed at said outlet.

14. An apparatus according to claim 13 wherein said mechanical means is adapted to reduce the volume of said cavity to a volume below about 1.5 milliliters.

15. An apparatus according to claim 13 wherein said mechanical means comprises a sleeve adapted to be moved from a position outside said cavity to a position inside said cavity.

16. An apparatus according to claim 15 wherein said sleeve comprises a deactivated glass sleeve.

17. An apparatus according to claim 13 wherein said analyzing means comprises a detector capable of detecting said at least one pyrolysis product of said sample, said detector selected from the group consisting of photocell detectors, thermocouple detectors and electron capture detectors.

18. An apparatus according to claim 13 wherein said vaporizing means comprises pyrolyzing means and wherein said at least one vaporization product comprises at least one pyrolysis product.

19. An apparatus according to claim 13 wherein said analyzing means comprises a mass spectrometer.

* * * * *

UNITED STATES PATENT AND TRADEMARK OFFICE
CERTIFICATE OF CORRECTION

PATENT NO. : 5,472,670
DATED : December 5, 1995
INVENTOR(S) : Peter de B. Harrington, et al.

It is certified that error appears in the above-indentified patent and that said Letters Patent is hereby corrected as shown below:

In column 2, line 1, please delete "he" and replace it with -- the --.

In column 2, line 28, after "cases," please add --it-- .

In column 3, line 11, please delete "amounts" and replace it with -- amount--.

In column 3, line 17, please delete "to".

In column 3, line 19, after "able" please add --to-- .

In column 5, line 12, please delete "is" and replace it with --of--.

In column 5, line 54, after "outside" please add --of--.

In column 6, line 19, after "outside" please add --of-- .

In column 10, line 47, please delete "form" and replace it with --from--.

In column 10, line 52, after "times" please add --of--.

UNITED STATES PATENT AND TRADEMARK OFFICE
CERTIFICATE OF CORRECTION

PATENT NO. : 5,472,670
DATED : December 5, 1995
INVENTOR(S) : Peter de B. Harrington, et al.

It is certified that error appears in the above-indentified patent and that said Letters Patent is hereby corrected as shown below:

In column 12, line 62, delete "columns" and replace it with --column--.

Signed and Sealed this

Tenth Day of September, 1996

Attest:

BRUCE LEHMAN

Attesting Officer    Commissioner of Patents and Trademarks